United States Patent
Roos et al.

(10) Patent No.: US 10,678,066 B2
(45) Date of Patent: Jun. 9, 2020

(54) METHOD FOR DETERMINING AN USAGE INDEX VALUE FOR AN SINGLE-VISION OPHTHALMIC LENS

(71) Applicant: Essilor International, Charenton-Le-Pont (FR)

(72) Inventors: Alexandra Roos, Singapore (SG); Julien Hubert, Charenton Le Pont (FR); Catherine Derbois, Charenton Le Pont (FR); Maxime Boiffier, Charenton Le Pont (FR); Aude Carrega, Charenton Le Pont (FR)

(73) Assignee: Essilor International, Charenton-le-Pont (FR)

( * ) Notice: Subject to any disclaimer, the term of this patent is extended or adjusted under 35 U.S.C. 154(b) by 60 days.

(21) Appl. No.: 15/766,040

(22) PCT Filed: Oct. 7, 2016

(86) PCT No.: PCT/EP2016/074084
§ 371 (c)(1),
(2) Date: Apr. 5, 2018

(87) PCT Pub. No.: WO2017/060480
PCT Pub. Date: Apr. 13, 2017

(65) Prior Publication Data
US 2018/0284479 A1 Oct. 4, 2018

(30) Foreign Application Priority Data

Oct. 9, 2015 (EP) .................................. 15306600

(51) Int. Cl.
*G02C 7/02* (2006.01)
*G02C 7/04* (2006.01)
(Continued)

(52) U.S. Cl.
CPC ............... *G02C 7/027* (2013.01); *G02C 7/02* (2013.01); *G02C 7/022* (2013.01); *G02C 7/04* (2013.01); *A61B 3/00* (2013.01); *G02C 13/003* (2013.01)

(58) Field of Classification Search
CPC . A61B 3/00; G02C 7/027; G02C 7/04; G02C 7/022; G02C 7/02; G02C 13/003
(Continued)

(56) References Cited

U.S. PATENT DOCUMENTS

| 6,231,182 B1 | 5/2001 | Guilino et al. |
| 2008/0084535 A1 | 4/2008 | De Ayguavives et al. |
| 2010/0003508 A1 | 1/2010 | Arrouy et al. |

FOREIGN PATENT DOCUMENTS

| DE | 195 40 186 A1 | 4/1997 |
| EP | 0 964 285 A1 | 12/1999 |

OTHER PUBLICATIONS

International Search Report dated Mar. 1, 2017 in PCT/EP2016/074084 filed Oct. 7, 2016.

*Primary Examiner* — Tuyen Tra
(74) *Attorney, Agent, or Firm* — Oblon, McClelland, Maier & Neustadt, L.L.P.

(57) ABSTRACT

The invention relates to a method for determining an usage index value for an single-vision ophthalmic lens adapted to correct the vision of a myopic wearer. According to the invention the method comprises: an optical profile providing step S1 during which an optical profile of said ophthalmic lens is determined; a material profile providing step S2 during which a material profile of said ophthalmic lens is determined; a physical parameter determining step S3 during which at least one physical parameter among physical parameters of said optical profile and material profile is determined; a gain assessing step S4 during which at least two gains brought by at least one determined physical (Continued)

parameter is evaluated on at least one evaluation criterion of dissatisfaction of said wearer when wearing said ophthalmic lens; an usage index value determining step S5 during which a value of an usage index is determined by adding the assessed gain for the evaluation criteria.

15 Claims, 1 Drawing Sheet

(51) Int. Cl.
*A61B 3/00* (2006.01)
*G02C 13/00* (2006.01)

(58) Field of Classification Search
USPC ....... 351/41, 159.01, 159.73, 159.74, 159.75
See application file for complete search history.

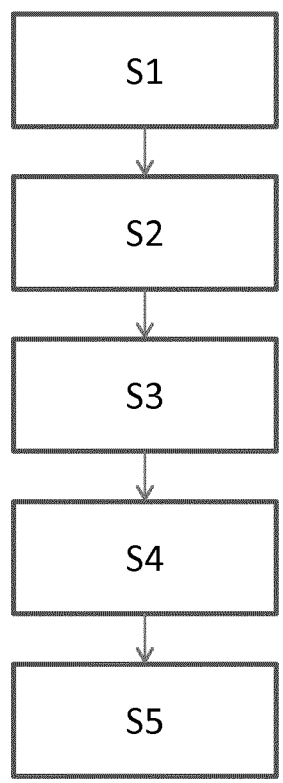

METHOD FOR DETERMINING AN USAGE INDEX VALUE FOR AN SINGLE-VISION OPHTHALMIC LENS

FIELD OF THE INVENTION

The present invention relates generally to a method for determining an usage index for an single-vision ophthalmic lens dedicated to the correction of myopia of an eye of a wearer, said usage index being representative of the satisfaction of the wearer when he wears the lens, and an single-vision ophthalmic lens of negative power, said lens ensuring aesthetics and enhanced wearing comfort to the wearer particularly in comparison with known single-vision ophthalmic lenses.

BACKGROUND OF THE INVENTION

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

Although high rates of myopia have been reported in some Asian areas for years, recent publications have highlighted the importance of and increases in this condition throughout Asia, as well as in the US and in Europe. As a result, the number of myopic people is expected to exceed a quarter of the world's population by 2020. Further affecting daily life, vision quality loss is the biggest concern raised due to an expected increase in myopia severity associated with higher risks of eye pathologies and blindness. However, some myopic people do not wear their correction lenses because of lack of wearing comfort and aesthetic issues.

Aesthetic problems caused by myopic lenses are numerous: a person who observes a myopic person equipped with a pair of spectacles comprising traditional corrective lenses perceives a jump of the image through the lens on their edge on the temporal side. Otherwise, the thickness of the edges of a negative power lens rapidly increases with optical power of the lens. Beyond its unsightly aspect, the high lens thickness causes also comfort problems due to an overweight of the lens.

For overcoming problems caused by lenses having thick edges, myopes may choose small size lenses. In this case, the man skilled in the art who advises a myope for choosing his/her ophthalmic equipment is restricted in the panel of spectacle frame he can propose in combination with small size lenses and thick edge lenses.

To date, over 40% of the corrective lens wearers of myopia are dissatisfied with the lenses they wear. The ophthalmic lenses according to the invention can satisfy at least 45% of wearers. This is highlighted into a gain in the usage index assigned to ophthalmic lenses according to the invention in comparison to usage index assigned to state of the art negative power ophthalmic lenses.

Therefore, it appears that there is a need to provide a method of providing a multifactor on satisfaction (or dissatisfaction) of a myopic wearer when wearing an ophthalmic lens.

SUMMARY OF THE INVENTION

To this end, the invention proposes a method, implemented by computer means, for determining an usage index value for an single-vision ophthalmic lens adapted to correct the vision of a myopic wearer, characterized in that it comprises:

an optical profile providing step (S1) during which an optical profile of said ophthalmic lens is determined;

a material profile providing step (S2) during which a material profile of said ophthalmic lens is determined;

a physical parameter determining step (S3) during which at least one physical parameter among physical parameters of said optical profile and material profile is determined;

a gain assessing step (S4) during which at least two gains brought by at least one determined physical parameter is evaluated on at least one evaluation criterion of dissatisfaction of said wearer when wearing said ophthalmic lens;

an usage index value determining step (S5) during which a value of an index value is determined by adding the assessed gain for the evaluation criteria.

Advantageously, said single-vision ophthalmic lens has a negative refractive power and is adapted for correcting vision of myopic people.

Advantageously, said at least one evaluation criterion is selected from the physical comfort of the wearer, the visual comfort of the wearer, appearance of the wearer, the aesthetics of the wearer, the wearer's eyestrain and the lens renewal factor.

Advantageously, said at least one physical parameters is selected from the shape of the surfaces of the two faces of the lens, the width of an optical field of view of said lens, the optical transmission of the lens over the visible spectrum, the edge thickness of the lens, the mean light reflection factor (Rv) of the lens over the visible spectrum, the chroma of the light reflected by the lens when arriving on the lens at an incident angle of 15°, the weight of said lens, the refractive index of the lens substrate, the size of the ophthalmic lens as edged to fit into a spectacle frame, the value of the hue angle of the lens at an angle of incidence less than or equal to 30°.

Said wearer being initially provided with a first pair of glasses comprising a first ophthalmic lens, said first wearer wishing to replace said first ophthalmic lens by a second lens.

Advantageously, a method for assisting the choice of an ophthalmic lens by a wearer comprises:

a step of determining a value of a first usage index, in which a method of determining a usage index value according to one of the preceding claims is applied to said first lens;

a step of determining at least a second usage index during which a method of determining a usage index value according to one of the preceding claims is applied to a second ophthalmic lens;

a step of providing an ophthalmic lens, during which the second ophthalmic lens is supplied to the wearer, where the value of said second usage index is greater than the value of said first usage index.

Advantageously, said first and second lenses are single-vision ophthalmic lenses.

Advantageously, said first and second lenses have an identical negative refractive power.

An object of the invention is therefore to remedy the above drawbacks, by seeking to develop an ophthalmic lens, comprising a substrate in organic material comprising at least an antireflective coating, said antireflective coating possessing very good antireflective performances in the visible region, while guarantying both good aesthetics whatever the angle of incidence of light.

The invention therefore relates to an ophthalmic lens, comprising a transparent substrate with a front face and with a rear face, at least one of said faces being coated with a multilayered antireflective coating comprising a stack of at least one layer having a refractive index higher than or equal to 1.5 and at least one layer having a refractive index lower than 1.5, such that:

the mean light reflection factor in the visible region Rv is lower than or equal to 0.5%, preferably equal or lower than 0.4%, more preferably equal or lower than 0.3% for an angle of incidence lower than 35°, typically for an angle of incidence of 15°;

the Chroma C* is higher than or equal 18, preferably higher than or equal 20, according to the international colorimetric CIE L*a*b* for an angle of incidence of 15° (generally for an angle of incidence from 0° to 25°, in particular for an angle of incidence from 0° to 20°).

The invention also relates to a single-vision ophthalmic lens of negative refractive power which comprises:

an optical profile including a double aspherical lens having:
  a front face having an aspherical surface;
  a rear face having an aspherical surface;
  a material profile comprising:
  a substrate of refractive index greater than or equal to 1.56;
  an antireflection coating having a mean light reflection factor in the visible region Rv smaller than or equal to 0.5%,
  an antistatic coating having a thickness smaller than 10 nm;
  a hydrophobic coating having a contact angle with water greater than 112°.

Advantageously, the refractive index of said substrate is greater than or equal to 1.60; and
  said antireflection coating has also:
  a hue angle (h) comprised between 260° and 325°, preferably between 275° and 325°, preferably between 290° and 310° for an angle of incidence smaller than or equal to 30°; and
  said antireflection coating is such that:
  a light reflecting on the lens with an incidence angle of 15° has a chroma (C*) greater than or equal to 15, preferably greater than or equal to 20.

Advantageously, said material profile further comprises an anti abrasion coating layer whose refractive index is adjusted to the substrate refractive index.

Advantageously, said lens further comprises a selective filtering means including at least one compound selected from dye, pigment, optical brightner and absorber which are able to absorb or emit specific range of wavelengths comprising UV light and/or the blue-violet light, and/or blue light, and/or near-infrared light and/or optionally comprises tint functions which may be passive or active such as photochromic tint, electrochromic tint and/or optionally polarized functions.

Advantageously, at least one of the aspherical surfaces of said lens has a rotational symmetry.

Advantageously, at least one of the aspherical surfaces is determined such that it is adapted individually to the wearing conditions of said wearer.

The ophthalmic lens of the invention enables to provide a technical solution to the problems caused by each of the evaluation criteria taken into account in the usage index determination.

Advantageously, an adapted combination of technical means used in the lens of the invention can meet the expectations of myopic wearers by optimizing the overall usage index. By convention one may consider that the optimum lens corresponds to the lens having the highest value of usage index. This highest value of usage index may be reached by considering a tradeoff between the considered gains over the various evaluation criterion.

BRIEF DESCRIPTION OF THE DRAWINGS

The invention will be better understood and illustrated by means of the following embodiments and execution examples, in no way limitative, with reference to the appended unique figure on which FIG. 1 is a flow chart of a method according to an embodiment of the invention.

DETAILED DESCRIPTION OF PREFERRED EMBODIMENTS

The invention relates to a method, for example implemented by computer means, for determining an usage index for an ophthalmic lens adapted to correct the vision of a myopic wearer. The ophthalmic lens is typically a single-vision negative power ophthalmic lens adapted to be mounted in a spectacle frame to be worn by the wearer. The lens being disposed in front of one of the wearer eyes when the spectacles are worn.

As represented on FIG. 1, the method according to the invention comprises at least:
  an optical profile providing step S1;
  a material profile providing step S2;
  a physical parameter measuring step S3;
  a gain assessing step S4;
  an usage index value evaluating step S5.

An optical profile of the lens is provided during the optical profile providing step.

The lens optical profile comprises at least one physical parameter of the lens qualifying the vision correction brought by the lens for a given substrate refractive index.

In an embodiment, the optical profile of the lens comprises a first and a second shape: the first shape being the shape of the front face of the lens and the second shape being the shape of the rear face of the lens.

In an embodiment, the first shape is an aspherical shape or a spherical shape or a toric shape.

In an embodiment, the second shape is an aspherical shape or a spherical shape or a toric shape.

In an embodiment, the first shape is rotationally asymmetrical.

In an embodiment, the second shape is rotationally asymmetrical.

An material profile of the lens is provided during the material profile providing step.

The lens material profile comprises at least one physical parameter qualifying the material found on the lens, substrate and coatings.

In an embodiment, the material profile of the lens comprises:
  a value of a refractive index of the lens substrate; and/or
  a value of a mean light reflection factor (Rv) in the visible region of an anti-reflection coating disposed on the lens; and/or
  a value of the thickness of an antistatic coating disposed on the lens; and/or
  a value of a contact angle of an hydrophobic coating disposed on the lens.

At least one physical parameter among the physical parameters of said optical profile and material profile is measured or determined during the physical parameter measuring step.

For example, the weight of the lens may be measured directly. The lens geometry (lens contour shape after edging) may also be provided by a frame manufacturer.

At least one gain brought by at least one determined physical parameter is evaluated on at least one evaluation criterion of dissatisfaction of said wearer when wearing said ophthalmic lens during the gain assessing step.

For example, the usage index is determined by evaluating at least six evaluation criteria:

Physical comfort, expressed as a source of dissatisfaction by wearers, notably for the following reasons:
  poor positioning of the lens in front of the eye;
  instability of the lens when placed in front of the eye (sliding lens);
  weight of the lens.

Visual comfort, expressed as a source of dissatisfaction by wearers, notably for the following reasons:
  restriction of the overall field of view of the wearer eye due to the small lens dimension and associated spectacle frame;
  non-optimal vision through the lens due to the presence of spherical aberration;
  discomfort of vision due to bad position of the eye on the equipment causing spatial shift of the effective correction;

Appearance of the eyes as seen by an observer, expressed as a source of dissatisfaction by wearers, notably for the following reasons:
  unnatural perception of the shape, size and color of the eyes;
  face deformation when seen through the lens resulting in a discontinuity of the face on the temporal sides of the lens;

Aesthetics, expressed as a source of dissatisfaction by wearers, notably for the following reasons:
  edge lens thickness;
  poor fit between the base of the lens and the base of the frame; the bases of the frames are typically 4 and those of the single vision lens for correction of myopia are usually to 2;
  transparency and residual reflection colour;
  presence of dust and/or dirt on the lens giving the impression of "dirty glasses"

Eyestrain expressed, as a source of dissatisfaction by wearers, notably for the following reasons:
  reduced fields of vision width between iso-power lines;
  difficulty of cleaning the lens leaving a scattering disturbing wearer sight;

Replacement of equipment, expressed as a source of dissatisfaction by wearers, notably for lack of frame adapted to the wearer.

These six criteria are linkable to the physical parameters of the optical profile and the material profile of the lens intended to equip a frame of a myopic wearer.

The physical comfort may result directly from measurable physical parameters of the lens such as lens weight, the position and size of the lens. E.g. the weightier is the lens, the lower is the gain in physical discomfort.

The appearance of the eyes as seen by an observer placed in front of a wearer of an lens may be evaluated by the shift of the temple of the wearer through the lens and the effective magnification of his/her eyes. The lens transparency may be quantified by measuring the lens transmittance (Tv), the mean light reflection factor (Rv), the chroma (C*) and hue angle (h) of the light reflected by the lens, especially under a specified angle of incidence. E.g. the higher the value of the mean light reflection factor is the lower is the gain in appearance.

Aesthetics may be measured via the determination of the lens base, the frame base, the thickness of the lenses including the lens edge thickness and by measurements of transmission and reflection properties of the lenses (Tv, Rv, C*, h), and the measures antistatic properties (conductivity) and hydrophobic properties (such as the contact angle with water) of the lens. E.g. the higher the value of the mean light reflection factor is the lower is the gain in aesthetics.

Eyestrain is particularly measurable from the iso-power lines shown on the lens, and the visual discomfort, which can cause visual fatigue perception due to the difficulty of cleaning the lenses may be quantified by measurement of the lens slide angle. E.g. the closer are the iso power lines, the lower is the gain in eyestrain.

Finally, the renewal of the related equipment including the reduced frames choice is measured directly via the geometry and size of lenses. For this criterion it is understood that an increase of the size of lens should not be realized if it causes an increase of other criteria of dissatisfaction, such as the criterion of physical comfort (particularly linked to the weight of the lens).

Finally, an usage index value is determined by adding the assessed gain for the evaluation criteria during the usage index value evaluating step.

This usage index value is for example expressed as a weighted sum of the assessed gain. The weight associated to an evaluation criterion may be personalized for taking into account the sensibility of the wearer on one particular evaluation criterion. For a wearer especially interested in his/her look, aesthetics and appearance may have for example a weight equal to 0.3, when eyestrain may have a weight equal to 0.1.

The method described above is particularly useful for providing assistance to wearers in the choice of the lens which is the most adapted to his/her needs.

Let's consider 3 different lenses (named below first, second and third lens) among which a myopic wearer has chosen one lens for correcting his/her vision at an Eye Care Professional (ECP) shop or on a website on internet. By carrying out the method according the invention successively on the first lens, the second lens and the third lens, one provides an usage index value for each of the three lenses. Then, based on the usage index value the wearer can easily identify the lens which fits the best his/her needs. By construction, it is the lens having the higher usage index.

This method is also useful when replacing a lens. The wearer first may determine the usage index of his/her current lens. Then he/she may choose his/her next lens among the available lens having an higher value of usage index.

For illustrating the invention, eyeware equipments comprising either ophthalmic lenses according to the invention or conventional single vision ophthalmic lenses are evaluated in a wearer test. The wearers performing the test have to assign at the end an usage index as defined above, by evaluating each tested lense according to the 6 criteria shown above. An example of results of such an multifactor evaluation is shown in the following table:

The more there is "+" in a cell of the third column, the greater the gain of dissatisfaction on the corresponding criterion is important.

| Criterion | Sub Criterion | Lens 1 |
|---|---|---|
| Physical Comfort | Lens position in respect with the nose | ++ |
| | Silding of the lens on the nose | ++ |
| | Lens Weight | +++ |

-continued

| Criterion | Sub Criterion | Lens 1 |
|---|---|---|
| Visual Comfort | Field of view limitations | ++ |
|  | Aberrations | +++ |
|  | Bad correction due to sliding | ++ |
| Appearance | Eye Shape and Eye color | ++ |
|  | Face deformation | ++ |
| Aesthetics | Lens Edge thickness | +++ |
|  | Lens base/Frame base Fit | ++ |
|  | Lens transparency and lens tint | ++ |
|  | Dust | +++ |
| Visual Fatigue | Field of view width (between is power) | +++ |
|  | Dirty lens (scattering) | +++ |
| Renewal | Limited Frame choice | +++ |

For each sub criterion, the number of '+' is counted and the corresponding usage index value is then:

$$UI_{Lens\ 1}=(2+2+3+2+3+2+2+2+3+2+2+3+3+3+3)=37$$

A second illustration of the method according to the invention is described below: very briefly speaking it differs from the example shown above in that each creiterion is beforehand weighted and the sum of "+" on each line of the array described above is also weighted for taking into account of the relative importance of each of the criterion for the wearers. The way these weights are assigned is derived from a paper written by Patrice Temblay and Benjamin Beauregard: «Application du modéle Tétraclasse aux resultatsde sondage d'un organisme public: le cas de la régie des rentes au Québec» Sept. 2006 Régie des rentes du Quebec Centre d'expertise des grands organismes. This paper presents how to apply a tool to measure a customer satisfaction: the model tetra was presented for the first time in 1997 by Sylvie Llosa. The practical grounds of this model are based on the theory of asymmetric contributions of factors to satisfaction. Asymmetric models are advantageous when compared to conventional models (or symmetric), especially because they allow to specify the impact of certain dimensions on satisfaction or dissatisfaction.

For our purpose, all the criterion listed in the first column above are sorted into 4 groups. Each group gathering criteria having similar importance according to 2 orthogonal axis: e.g. a first (e.g. vertical) axis shows the "impact of the criterion on satisfaction" a second (e.g. horizontal) axis shows the "impact of the criterion on dissatisfaction". According to this representation, a plan may be split into 4 sectors: criteria may be located on this plane in respect with these axis according to large qualitative wearer studies. A first group to consider is the group of criteria having the higher impact on the satisfaction AND the higher impact on dissatisfaction. A second group to consider is the group of criteria having the lower impact on the satisfaction AND the higher impact on dissatisfaction. A third group to consider is the group of criteria having the higher impact on the satisfaction AND the lower impact on dissatisfaction. A fourth group to consider is the group of criteria having the lower impact on the satisfaction AND the lower impact on dissatisfaction.

By assigning all the sub criteria in relation with the criteria belonging to the first group with the weight 4, all the sub criteria in relation with the criteria belonging to the second group with the weight 3, all the sub criteria in relation with the criteria belonging to the third group with the weight 2, all the sub criteria in relation with the criteria belonging to the fourth group with the weight 1, one gets a usage index more representative of the needs of the wearer.

For example if 'Physical comfort' is weighted with 4, visual comfort is weighted with 4, aesthetics is weighted with 3, the 'Visual Fatigue' is weighted with 2, the usage index calculated by considering these corresponding weights allows to compare easily and more accurely two different lenses: for example a traditionnal lens and one of the lenses according to the invention described below. This a surprising advantage of this method to provide a multi factor index adapted to the needs and the aspirations of a particular population.

A lens of the invention comprises:

double aspherical lens (with first and second shape are aspherical shape) enabling to achieve a thinner and therefore lighter, flatter lens than state of the art lenses and also with less spherical aberrations;

a lens substrate having a refractive index greater than or equal to 1.56, or greater than or equal to 1.6, preferably greater than or equal to 1.67, to achieve lighter and thinner lens than state of the art lenses.

Ophthalmic lenses according to the invention can be used to improve the visual perception of a wearer and/or to improve viewing comfort.

The better performance in weight and thickness produces thus a gain on the usage index by impacting each of the 6 evaluation criteria considered above.

Such a lens has also a better fit on the wearer face. The sliding is limited and then improves physical and visual comfort. The lens position stability limits the spatial offset of the effective correction and then the wearer has when looking through the lens the optical power to gaze straight ahead.

This gain in weight and thickness enables to consider making larger lenses, opening the range of frames available capable of receiving these glasses. A wider offer represents a relevant factor to increase the turnover rate of the lens, it has a direct benefit for the wearer.

In the present application, a coating that is "on" a substrate/coating or which has been deposited "on" a substrate/coating is defined as a coating that (i) is positioned above the substrate/coating, (ii) is not necessarily in contact with the substrate/coating, that is to say that one or more intermediate coatings may be disposed between the substrate/coating and the coating in question (although it is preferably contacting said substrate/coating).

When "a layer 1 is shown under a layer 2", it is understood that the layer 2 is further from the substrate than the layer 1. Similarly a layer called "outer" is further from the substrate a layer called "internal".

An antireflective coating is defined as a coating, deposited on the surface of an article, which improves the antireflective properties of the final article. It can reduce the reflection of light to article-air interface over a relatively large portion of the visible spectrum. Preferably Rv, the average reflection factor of light, is smaller than 2.5% per side.

Rv is defined in the ISO13666: 1998 standard and measured according to ISO 8980-4 (for an angle of incidence of the light smaller than 17°, typically smaller than 15°). Rv is preferably smaller than 2%, most Rv is smaller than 1.5% and even better Rv is smaller than 1%. As is also well known, the antireflection coatings typically comprise a monolayer or multilayer stack of dielectric materials. They are preferably multilayer coatings comprising layers of high refractive index (HI) and layers of low refractive index (BI).

The formation of such coatings, their thickness and deposit method are described in particular in patent application WO 2010/109154.

It is admitted that the light rays that may reflect onto the lens rear face and reach the wearer's eye have a narrow incidence angle range, ranging from 30° to 45° (oblique incidence).

In addition, depending on the curvatures of the lenses and the value of incidence, the residual reflected color of the multilayered anti reflective coating of each lens seems not to be homogeneous in color on all the surface of the lens ("chameleon effect"). A different residual reflected color between the right and the left portions of a lens, such as a color gradient of different hues "h" (not the same color turning for instance from blue to red) or a color gradient of different color intensity (for example, turning from saturated color to a less saturated color, or inversely) may be viewed by an observer according to the incidence angle δ. Hence, it would be desirable to improve the aesthetic appearance of such a lens by obtaining, for instance, a homogenous perceived residual reflected color of the lens surface for an observer looking at the lens wearer.

Therefore, there is still a need to provide novel antireflective coatings having very good antireflective properties at least in the visible region and possibly in the UVA and UVB bands, while having at the same time robustness properties and aesthetic appearance whatever the angle of incidence versus the antireflective coatings of the prior art.

Without being bound by any theories, it seems that the anti reflective coating according to the invention has a residual reflected color which is sufficient saturated color, so as overcome the variations of the perceived residual reflected color of said antireflective coating (by an observer) between two lenses (comprising said antireflective coating) which may arise during the manufacturing process, especially at industrial scale.

Preferably, the multilayered antireflective coating has a hue (h) from 275° to 325°, preferably from 280° to 320°, more preferably from 290° to 318°, typically from 295° to 315°, in particular from 298° to 314° and for instance from 300° to 305° according to the international colorimetric CIE L*a*b* for an angle of incidence less than or equal to 35°, preferably lower 25° than or equal 30°, in particular lower than or equal 25° and typically lower than or equal 20°.

Hence, the antireflective coating of the present invention shows smooth perceived residual color variation according to the angle of incidence.

As it will be illustrated in the examples below, the hue h of the antireflective coating is substantially constant, that is to say typically between 280° to 320° and in particular between 295° to 315°, for an angle of incidence varying from 0° to 30°. Indeed, the perceived residual reflected color when the angle of incidence varying from 0° to 30° is the "same" for an observer having a normal vision. When the hue of the antireflective coating begins to vary for an angle of incidence higher than 30°, the Chroma C* is very low (lower than or equal to 11), that is to say the perceived residual reflected color is very pale such that the residual reflected color is not perceptible or hardly noticeable for an observer. Hence, the residual reflected color of the antireflective coating of the lens according to the invention is homogeneous whatever the angle of incidence. Therefore, it has good aesthetic performances (smooth color variation according to the angle of incidence).

The optical article of the invention may be made antistatic, that is to say not to retain and/or develop a substantial static charge, by incorporating at least one charge dissipating conductive layer into the stack present on the surface of the article.

As used herein, an "electrically conductive layer" or an "antistatic layer" is intended to mean a layer which, due to its presence on the surface of a non-antistatic substrate (i.e. having a discharge time higher than 500 ms), enables to have a discharge time of 500 ms or less after a static charge has been applied onto the surface thereof. Typically in accordance with the invention, the ophthalmic of the invention comprised an antistatic layer which is preferentially incorporated to the anti-reflective coating. Advantageously the antistatic layer is a layer of $SnO_2$ or ITO (Indium Tin Oxyde) with a thickness layer less than 10 nm.

The antistatic layer is preferably located between two layers of the antireflective coating, and/or is adjacent to a layer with a high refractive index of such antireflective coating. Preferably, the antistatic layer is located immediately under a layer with a low refractive index of the antireflective coating, most preferably is the penultimate layer of the antireflective coating by being located immediately under the low refractive index outer layer of the antireflective coating.

In a specific embodiment, the antistatic layer is part of a bilayer having a thickness of 60 nm or less, preferably 30 nm or less, composed of a low refractive index layer and said antistatic layer, said antistatic layer being in direct contact with the low refractive index outer layer of the antireflection coating.

Typically, the antireflective coating comprises, starting from the surface of the substrate optionally coated with one or more functional coatings and coated preferably with a 100 to 200 nm-thick sub-layer, preferably of silica, a layer with a high refractive index with a thickness from 14 to 22 nm, preferably of zirconia, a layer with a low refractive index with a thickness of from 27 to 32 nm, preferably of silica, a layer with a high refractive index with a thickness of from 68 to 100 nm, preferably of zirconia, optionally an electrically conductive layer with a thickness of from 4 to 8 nm, and a layer with a low refractive index with a thickness of from 87 to 95 nm, preferably of silica. The sub-layer, which has no optical function but only mechanical function, may comprise a sole layer of silica, or may comprise more than one layer wherein low refractive index layer and high refractive index layer are alternated. In such case the sub-layer may comprise for example a first thin layer (less than 50 nm) of silica, then a second thin layer of zirconia (less than 15 nm), then a thick layer of silica (from 80 nm to 130 nm).

The hydrophobic surface coatings are mainly obtained from polymerizable compositions comprising at least one fluorinated compound, more preferably at least one silane compound nature and/or silazane bearing one or more fluorine groups, especially fluorinated hydrocarbon groups, perfluorocarbon, fluorinated polyether group such as $F_3C(OC_3F_6)_{24}$—O—$(CF_2)_2$—$(CH_2)_2$—O—$CH_2$—$Si(OCH_3)_3$ or perfluoropolyether.

Commercial compositions for the preparation of hydrophobic coatings are compositions KY130® (the formula of the patent JP 2005-187936) and KP 801M® marketed by Shin-Etsu Chemical, OF210 and OF110™ marketed by Optron, and composition OPTOOL DSX® (a fluorinated resin comprising perfluoropropylene groups having the formula of U.S. Pat. No. 6,183,872) commercialized by Daikin Industries. The composition OPTOOL DSX® is the preferred anti-smudge coating composition.

The ophthalmic lens of the invention comprises an anti-abrasion layer which is able to improve scratch and impact resistance of said lens. Advantageously, the anti-abrasion layer may present a refractive index closed to the refractive index of the substrate, it means for example than for a substrate with a refractive index of at least 1.6, the refractive index of said anti-abrasion layer will be 1.6. Such anti-abrasion layer is well known to the prior art, and as example, particularly suitable anti-abrasion for the present invention is as mentioned to EP0614957 and WO2013/004954. In another embodiment, the present invention comprised advantageously a quarter waveplate layer interposed between the substrate and the anti-abrasion layer, such quarter waveplate layer being able to minimize interference fringes which occurs generally when substrate and anti-abraison layer are not the same refractive index. Such quarter waveplate are notably described to US2004/0074261.

Hereafter Lens 1 and Lens 2 are two examples of lenses accroding to the invention.

Lens 1 and Lens 2 have an optical profile comprising a double aspherical single vision lens, having an optical power smaller or equal to −0.25 dioptrie.

The material profile of Lens 1 comprises also a substrate in Stylis® material with refractive index equal to 1,67, Tv=96%, Rv=0,49%, C*=10,5, h=260°, water contact angle on front face: 112°;

The AR layer of Lens 1 comprises:
A sub layer of $SiO_2$ having a width equal to 137.9 nm;
A first layer of $ZrO_2$ having a width equal to 17.1 nm;
A second layer of $SiO_2$ having a width equal to 28.3 nm;
A third layer of $ZrO_2$ having a width equal to 96.5 nm;
An antistatic layer of ITO having a width equal to 6.5 nm;
A fourth layer of $SiO_2$ having a width equal to 91.0 nm.

The material profile of Lens 2 comprises a substrate in Stylis® material with refractive index equal to1,67, Tv=96%, Rv=0,3%, C*=24,8, h=300°, water contact angle: 114°;

The AR layer of Lens 2 comprises:
A sub layer of $SiO_2$ having a width equal to 150 nm
A first layer of $ZrO_2$ having a width equal to 12.2 nm
A second layer of $SiO_2$ having a width equal to 28.76 nm
A third layer of $ZrO_2$ having a width equal to 87.98 nm
An antistatic layer of ITO having a width equal to 6.5 nm
A fourth layer of $SiO_2$ having a width equal to 89.32 nm The reflection mean factor values are those of the front face. The factors Rv, is provided for an angle of incidence of 15° and the colorimetric coefficients of the optical article of the invention in the international colorimetric system CIE L*a*b* are calculated between 380 and 780 nm, taking into account the observer (standard observer) and the standard illuminant D 65 at an angle of incidence equal to 15° for C* and less or equal to 30° for h.

| Layer (physical thickness in nm) | Lens 1 (Fabrication) | Lens 2 (Calculated) | Lens 2 (Fabrication) |
| --- | --- | --- | --- |
| Air | | | |
| $SiO_2$ | 91.0 | 89.28 | 89.32 |
| ITO | 6.5 | 6.5 | 6.5 |
| $ZrO_2$ | 96.5 | 88 | 87.98 |
| $SiO_2$ | 28.3 | 28.94 | 28.76 |
| $ZrO_2$ | 17.1 | 15.47 | 15.2 |
| Sub layer ($SiO_2$) | 137.9 (*) | 150 | 150 |
| $R_V$ | 0.49% | 0.30% | 0.30% |
| h° (incidence angle: 30°) | 260 | 300 | 300 |
| C* (incidence angle: 15°) | 10.5 | 24.8 | 24.8 |

(*) For Lens 1, the sub layer comprises a third layer of SiO2 and two impedance layers of ZrO2 and SiO2 which are closed to the anti abrasion layer.

It is to be understood that the figures and descriptions of the present invention have been simplified to illustrate elements that are relevant for a clear understanding of the present invention, while eliminating, for purposes of clarity, many other elements found in typical digital multimedia content delivery methods and systems. However, because such elements are well known in the art, a detailed discussion of such elements is not provided herein. The disclosure herein is directed to all such variations and modifications known to those skilled in the art.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

Reference herein to "one embodiment" or "an embodiment" means that a particular feature, structure, or characteristic described in connection with the embodiment can be included in at least one implementation of the invention. The appearances of the phrase "in one embodiment" in various places in the specification are not necessarily all referring to the same embodiment, nor are separate or alternative embodiments necessarily mutually exclusive of other embodiments.

The invention claimed is:

1. A method for assisting the choice of an ophthalmic lens by a wearer, said wearer being initially provided with a first pair of glasses comprising a first ophthalmic lens, said wearer wishing to replace said first ophthalmic lens with a second ophthalmic lens, wherein the method comprises:

determining a value of a first usage index;

determining at least one second usage index;

providing an ophthalmic lens comprising supplying the second ophthalmic lens to the wearer, where the value of said second usage index is greater than the value of said first usage index;

wherein determining a value of the first usage index comprises:

determining a first optical profile of said first ophthalmic lens;

determining a first material profile of said first ophthalmic lens;

determining at least one first physical parameter among physical parameters of said first optical profile and first material profile;

comprising evaluating at least two first gains brought by at least one determined first physical parameter on at least one first evaluation criterion of dissatisfaction of said wearer when wearing said first ophthalmic lens; and determining a value of a first usage index by adding the assessed first gain for the first evaluation criteria;

wherein determining a value of the second usage index comprises:

determining a second optical profile of said second ophthalmic lens;

determining a second material profile of said second ophthalmic lens;

determining at least one second physical parameter among physical parameters of said second optical profile and first material profile;

comprising evaluating at least two second gains brought by at least one determined second physical parameter on at least one second evaluation criterion of dissatisfaction of said wearer when wearing said second ophthalmic lens; and determining a value of a second usage index by adding the assessed second gain for the second evaluation criteria.

2. The method according to claim 1, wherein said first and second ophthalmic lenses are single-vision ophthalmic lenses.

3. The method of claim 1, wherein said first and second ophthalmic lenses have an identical negative refractive power.

4. A single-vision ophthalmic lens of negative refractive power comprising:
a substrate having:
a front face having an aspherical surface;
a rear face having an aspherical surface; and
a refractive index greater than or equal to 1.56;
an antireflection coating having a mean light reflection factor in the visible region Rv smaller than or equal to 0.5% on the front or rear face;
an antistatic coating having a thickness smaller than 10 nm on the front or rear face; and
a hydrophobic coating having a contact angle with water greater than 112° on the front or rear face.

5. The single-vision ophthalmic lens of claim 4, wherein:
the refractive index of said substrate is greater than or equal to 1.60; and
said antireflection coating is such that a light reflecting on the lens with an incidence angle of 30° has also a hue angle (h) comprised between 260° and 325°; and
said antireflection coating is such that a light reflecting on the lens with an incidence angle of 15° has a chroma (C*) greater than or equal to 15.

6. The single-vision ophthalmic lens of claim 5, wherein said antireflection coating is such that a light reflecting on the lens with an incidence angle smaller than or equal to 30° has also a hue angle (h) comprised between 290° and 310°.

7. The single-vision ophthalmic lens of claim 5, wherein antireflection coating is such that a light reflecting on the lens with an incidence angle of 15° has a chroma (C*) greater than or equal to 20.

8. The single-vision ophthalmic lens of claim 4, further comprising on the substrate an anti-abrasion coating layer with a refractive index adjusted to the substrate refractive index.

9. The single-vision ophthalmic lens of claim 4, further comprising a selective filter on the substrate.

10. The single-vision ophthalmic lens of claim 9, wherein the selective filter includes at least one compound chosen from the group consisting of dye, pigment, optical brightener and absorber which are able to absorb or emit specific range of wavelengths.

11. The single-vision ophthalmic lens of claim 10, wherein the specific range of wavelengths comprises at least one selected from UV light, the blue-violet light, blue light, and near-infrared light.

12. The single-vision ophthalmic lens of claim 9, wherein the selective filter comprises a passive or active tint function.

13. The single-vision ophthalmic lens of claim 12, wherein the passive or active tint function is at least one chosen from the list consisting of photochromic tint, electrochromic tint and polarized function.

14. The single-vision ophthalmic lens of claim 4, wherein at least one of the aspherical surfaces of said lens has a rotational symmetry.

15. The single-vision ophthalmic lens of claim 4, wherein at least one of the aspherical surfaces is determined such that it is adapted individually to the wearing conditions of a wearer.

* * * * *